(12) United States Patent
Bahal et al.

(10) Patent No.: US 11,833,254 B2
(45) Date of Patent: Dec. 5, 2023

(54) DISCOIDAL NANO UNIVERSAL PLATFORM FOR EFFICIENT DELIVERY OF PNAS

(71) Applicant: University of Connecticut, Farmington, CT (US)

(72) Inventors: Raman Bahal, Glastonbury, CT (US); Mu-Ping Nieh, Mansfield, CT (US); Armin Tahmasbi Rad, Manchester, CT (US); Shipra Malik, Storrs, CT (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 225 days.

(21) Appl. No.: 17/332,258

(22) Filed: May 27, 2021

(65) Prior Publication Data

US 2021/0369632 A1    Dec. 2, 2021

Related U.S. Application Data

(60) Provisional application No. 63/030,352, filed on May 27, 2020.

(51) Int. Cl.
*A61K 9/127* (2006.01)
*A61K 9/51* (2006.01)
(Continued)

(52) U.S. Cl.
CPC .......... *A61K 9/5123* (2013.01); *A61K 9/1271* (2013.01); *A61K 9/1274* (2013.01);
(Continued)

(58) Field of Classification Search
CPC .... A61K 9/1271; A61K 9/1274; A61K 9/145; A61K 9/146; A61K 9/51; A61K 9/5123;
(Continued)

(56) References Cited

U.S. PATENT DOCUMENTS

| 5,422,251 A | 6/1995 | Fresco |
| 10,221,216 B2 | 3/2019 | Ly et al. |

(Continued)

OTHER PUBLICATIONS

Gupta et al. Anti-tumor Activity of miniPEG-gamma-Modified PNAs to Inhibit MicroRNA-210 for Cancer Therapy. Molecular Therapy Nucleic Acids. Dec. 2017, vol. 9, pp. 111-119. (Year: 2017).*

(Continued)

*Primary Examiner* — Jeffrey E. Russel
(74) *Attorney, Agent, or Firm* — CANTOR COLBURN LLP

(57) ABSTRACT

A self-assembled discoidal PNA delivery vehicle includes a zwitterionic short chain diacyl lipid, a zwitterionic long chain diacyl lipid, a charged long chain diacyl lipid, a PEGylated lipid of the formula distearoyl phosphoethanolamine (DSPE)-PEG$_n$-TG, and an encapsulated PNA molecule with a defined molar ratio of the zwitterionic long chain diacyl lipid and the charged long chain diacyl lipid to the short chain diacyl lipid, the molar ratio of the charged long chain diacyl lipid to the zwitterionic long chain diacyl lipid, molar % of the PEGylated lipid to all lipids, and ratio of PNA to lipid. Also described are method of self-assembling the discoidal PNA delivery vehicle and methods of enhancing cellular uptake of PNA using the discoidal PNA delivery vehicle.

14 Claims, 8 Drawing Sheets
(7 of 8 Drawing Sheet(s) Filed in Color)
Specification includes a Sequence Listing.

(51) Int. Cl.

| | |
|---|---|
| *A61K 47/24* | (2006.01) |
| *A61K 47/34* | (2017.01) |
| *A61K 47/26* | (2006.01) |
| *A61K 47/42* | (2017.01) |
| *A61K 9/14* | (2006.01) |

(52) U.S. Cl.
CPC ............ *A61K 9/146* (2013.01); *A61K 9/5146* (2013.01); *A61K 9/5192* (2013.01); *A61K 47/24* (2013.01); *A61K 47/26* (2013.01); *A61K 47/34* (2013.01); *A61K 47/42* (2013.01)

(58) Field of Classification Search
CPC .... A61K 9/5146; A61K 9/5192; A61K 47/24; A61K 47/34
See application file for complete search history.

(56) References Cited

U.S. PATENT DOCUMENTS

| | | | |
|---|---|---|---|
| 10,793,605 | B2 | 10/2020 | Ly et al. |
| 2010/0015218 | A1 | 1/2010 | Jadhav et al. |
| 2010/0062067 | A1* | 3/2010 | Tonge ...................... B82Y 5/00 977/773 |
| 2010/0311844 | A1* | 12/2010 | Qi ........................ A61K 9/1272 514/773 |
| 2017/0283830 | A1 | 10/2017 | Saltzman et al. |
| 2018/0015174 | A1 | 1/2018 | Irvine et al. |

OTHER PUBLICATIONS

Rad et al. A universal discoidal nanoplatform for the intracellular delivery of PNAs. Nanoscale. Jul. 14, 2019, vol. 11, No. 26, pp. 12517-12529. (Year: 2019).*

Beales, P. et al.; "Application of nucleic acid-lipid conjugates for the programmable organization of liposomal modules"; Advances in Colloid and Interface Science, vol. 207; 2014; pp. 290-305; doi: 10.1016/j.cis.2013.12.009.

Iqbal, U. et al.; "Targeted MRI and Optical Molecular Imaging Using Gadolinium Loaded Small Unilamellar Vesicles"; 2011 AIChE annual meeting, Oct. 16-21, Minneapolis Convention Center, Minneapolis, MN; conference proceedings; Non-topical conferences; 9 pages.

Kumar, S. et al.; "Modular self-assembly of gamma-modified peptide nucleic acids in organic solvent mixtures"; Nature Communications, vol. 11, Issue No. 1; 2020; 10 pages; doi: 10.1038/s41467-020-16759-8.

Liu, et al.; "Stable Discoidal Bicelles: A Platform of Lipid Nanocarriers for Cellular Delivery"; Methods in Molecular Biology, vol. 1522; 2017; pp. 273-282; doi: 10.1007/978-1-4939-6591-5_22.

Loew, M. et al.; "Lipid Domain Specific Recruitment of Lipophilic Nucleic Acids: A Key for Switchable Functionalization of Membranes"; Journal of the American Chemical Society, vol. 132, Issue No. 45; 2010; pp. 16066-16072.

Nieh, M. et al.; "Spontaneously formed unilamellar vesicles" Methods in Enzymology, vol. 465; 2009; pp. 3-20; doi: 10.1016/S0076-6879(09)65001-1.

* cited by examiner

FIGs. 4A-J

SEQUENCE LISTING

```
<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<223> OTHER INFORMATION: Synthetic oligoucleotide
<220> FEATURE:
<221> NAME/KEY: modified_base
<222> LOCATION: (1)..(23)
<223> OTHER INFORMATION: Peptide nucleic acid

<400> SEQUENCE: 1
acccctatca cgattagcat taa                                              23

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(22)
<223> OTHER INFORMATION: Peptide nucleic acid
```

```
<400> SEQUENCE: 2
tcagccgctg tcacacgcac ag                                              22
```

DISCOIDAL NANO UNIVERSAL PLATFORM FOR EFFICIENT DELIVERY OF PNAS

CROSS-REFERENCE TO RELATED APPLICATIONS

This application claims priority to U.S. Provisional Application 63/030,352 filed on May 27, 2020, which is incorporated herein by reference in its entirety.

STATEMENT REGARDING FEDERALLY SPONSORED RESEARCH & DEVELOPMENT

This invention was made with government support under 1605971 awarded by the National Science Foundation. The government has certain rights in the invention.

BACKGROUND

Peptide nucleic acids (PNAs) have expanded widely from last few years not only for their role in basic research but also in therapeutic areas pertaining to gene editing and targeting. PNAs are artificial DNA mimics that consist of pyrimidine or purine nucleobases attached to a highly flexible pseudopeptide backbone. It has been well established that PNAs bind with high affinity to genomic DNA and RNA targets based on Watson Crick recognition principles and regulate gene expression. In addition, the neutral backbone of PNAs makes it resistant to enzymatic degradation. The aforementioned unique properties of PNAs make them attractive reagents for therapeutic and diagnostic applications. However, intracellular delivery is an enormous challenge.

Several promising chemical, mechanical and electrical transduction-based methods have been explored for increasing intracellular delivery of PNAs. However, these methods can only apply to small experimental conditions and cannot translate to in vivo studies as well as for clinical applications. Additionally, transduction reagents often lead to off-target and cytotoxic effects. Similarly, a series of cationic residue conjugated PNAs have been explored that could aid cellular uptake of PNAs by increasing their degree of interaction with negatively charge cell membrane. Though these strategies have shown promise up to a certain extent, the inclusion of cationic groups also increases cytotoxicity both in vitro as well as in vivo. Other possibilities of incorporating the transduction domain onto the achiral backbone of PNAs have been investigated. These include the development of guanidinium and lysine based chemically modified gamma PNAs. However, these methods require complicated synthetic procedures and elaborate optimization to generate ample material especially for in vivo studies.

Recently, nanoparticle (NP) based strategies have garnered attention to deliver PNAs, however, the strategies do not provide the payload of PNAs that is necessary for clinical efficacy. What is needed are novel delivery vehicles for PNA, particular those that provide clinically useful amounts of PNA.

BRIEF SUMMARY

In an aspect, a self-assembled discoidal PNA delivery vehicle comprises a zwitterionic short chain 5:0 to 7:0 diacyl lipid comprising a phosphatidylcholine or phosphatidylethanolamine hydrophilic headgroup; a zwitterionic long chain 14:0 to 18:0 diacyl lipid comprising a phosphatidylcholine or phosphatidylethanolamine hydrophilic headgroup; a charged long chain 12:0 to 18:0 diacyl lipid comprising a phosphatidylglycerol, phosphoinositol, phosphatidic acid, or phosphatidylserine hydrophilic headgroup; a PEGylated lipid of the formula distearoyl phosphoethanolamine (DSPE)-PEG$_n$-TG, wherein n is the molecular weight of the PEG and is 1000 to 5000, and TG is a terminal group which is hydroxyl, succinyl, cyanur, folate, maleimide, pyridoxal-5'-diphosphate (PDP), amine, biotin, trimethylsilyl (TMS), carboxylic acid, azide, dibenzocyclooctyne (DBCO), or benzylguanine; and an encapsulated PNA molecule; wherein the molar ratio of the zwitterionic long chain diacyl lipid and the charged long chain diacyl lipid to the short chain diacyl lipid is 0.5 to 5, wherein the molar ratio of the charged long chain diacyl lipid to the zwitterionic long chain diacyl lipid is greater than 0.01, wherein the molar % of the PEGylated lipid to all lipids is 1% to 5%, and wherein the ratio of PNA to total lipid is 1:500 to 1:2500.

In another aspect, a one pot method of self assembling a discoidal PNA delivery vehicle comprising encapsulated PNA comprising mixing a cosolvent and the above-described lipids and PNA, providing sufficient time for the discoidal PNA delivery vehicle to self assemble and encapsulate the PNA; and optionally removing the cosolvent.

In yet another aspect, a method of enhancing cellular uptake of PNA comprises contacting a cell with the above described self assembled discoidal PNA delivery vehicle, wherein the self assembled discoidal PNA delivery vehicle provides improved cellular uptake compared to a liposome.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above-described and other features will be appreciated and understood by those skilled in the art from the following detailed description, drawings, and appended claims.

DETAILED DESCRIPTION

Described herein are a low-polydispersity, spontaneously-forming discoidal bicelles (nanodiscs or NDs) with a diameter of approximately 30 nm and a thickness of 5 nm in a mixture of long- and short-chain lipids that have been employed for entrapping hydrophobic molecules with a robust membrane formation/assembly mechanism. The membrane-mimicking NDs are stabilized by polyethyleneglycol conjugated (PEGylated) lipids and easily incorporated with amphiphilic biomolecules such as membrane proteins making them an attractive system for solubilization, isolation, purification, and biophysical and biochemical studies of membrane proteins. The cellular uptake of NDs is approximately 5-10 times higher than spherical vesicles with an identical chemical composition, because they take more routes of internalization than the vesicles do. Enhanced uptake, more diverse mechanisms for endocytosis and faster diffusion across the membranes due to the small size make NDs a better candidate than the conventional polymeric and inorganic spherical nanocarriers.

Figure 1:
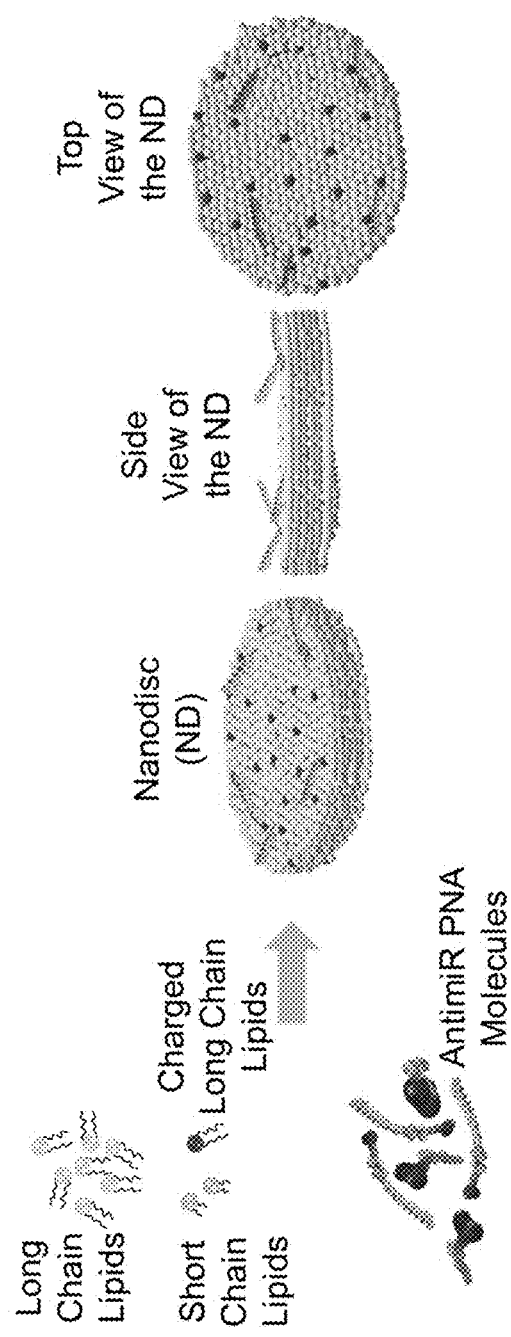
FIG. 1 is a schematic of the nanodiscs of the present disclosure.

As described herein, several ND/PNA nanocomplexes were characterized in structure and designed for optimal endocytotic delivery. FIG. 1 is a schematic of the NDs with entrapped PNA. The new class of nanocarrier shows excellent transfection efficiency with low toxicity and high payload. Herein, NDs were utilized for the delivery of antimiRs targeting miR-155 (PNA-155) and 210 (PNA-210). Comprehensive evaluation of loading capacity, size, morphology and efficacy of antimiR-155- and 210 PNA-containing NDs was performed. Additionally, molecular modeling, and small-angle X-ray scattering (SAXS) were performed to evaluate the interaction of hydrophobic PNAs with lipid. The transfection efficiencies of these NDs in cervical cancer cells (HeLa) were studied. The cellular uptake mechanism of NDs containing antimiR PNAs in HeLa cells was evaluated. The results highlight efficient and safe ND-mediated delivery of PNAs that can be used effectively for extensive biomedical applications.

The data demonstrate that PNAs can be efficiently delivered by NDs such as negatively charged NDs. This approach can be used to effectively reduce the levels of miRNA expression via an antisense mechanism. Improvements in accessibility to molecular targets and increased specificity could further be increased by coating PNA loaded NDs with specific peptides, antibody and carbohydrate units. In summary, described herein is a novel platform for PNA delivery that can be used for therapeutic purposes. The PNA/ND technology can be used to control the gene expression and regulation.

In an aspect, a self-assembled discoidal PNA delivery vehicle comprises a zwitterionic short chain 5:0 to 7:0 diacyl lipid comprising a phosphatidylcholine or phosphatidylethanolamine hydrophilic headgroup; a zwitterionic long chain 14:0 to 18:0 diacyl lipid comprising a phosphatidylcholine or phosphatidylethanolamine hydrophilic headgroup; a charged long chain 12:0 to 18:0 diacyl lipid comprising a phosphatidylglycerol, phosphoinositol, phosphatidic acid, or phosphatidylserine hydrophilic headgroup; a PEGylated lipid of the formula distearoyl phosphoethanolamine (DSPE)-PEG$_n$-TG, wherein n is the molecular weight of the PEG and is 1000 to 5000, and TG is a terminal group which is hydroxyl, succinyl, cyanur, folate, maleimide, pyridoxal-5'-diphosphate (PDP), amine, biotin, trimethylsilyl (TMS), carboxylic acid, azide, dibenzocyclooctyne (DBCO), or benzylguanine; and an encapsulated PNA molecule; wherein the molar ratio of the zwitterionic long chain diacyl lipid and the charged long chain diacyl lipid to the short chain diacyl lipid is 0.5 to 5, wherein the molar ratio of the charged long chain diacyl lipid to the zwitterionic long chain diacyl lipid is greater than 0.01, wherein the molar % of the PEGylated lipid to all lipids is 1% to 5%, and wherein the molar ratio of PNA to total lipid is 1:1 to 1:10000, specifically 1:500 to 1:2500.

The encapsulated PNA means that PNA is either entrapped in the bicellar interior or attached to the surface of bicelle.

In a specific aspect, the zwitterionic short chain diacyl lipid is a dihexanoyl phosphatidylcholine (DHPC) lipid, the zwitterionic long chain diacyl lipid is a dipalmitoyl phosphatidylcholine (DPPC) lipid, the charged long chain diacyl lipid is a dipalmitoyl phosphatidylglycerol (DPPG) lipid, and the pegylated lipid is a PEG2000-conjugated distearoyl phosphoethanolamine (DSPE-PEG2000).

In an aspect, the self-assembled discoidal PNA delivery vehicle has a diameter along the circular axis of 20-100 nm, specifically 20-50 nm. Advantageously, this size of ND is in the size range shown to have high accumulation at tumor sites (e.g., via the "enhanced permeability and retention", EPR, effect). The results herein show that using this nanocarrier to deliver the PNA, unexpectedly, enhances the cellular and tumor uptake significantly, which ultimately results in a more efficient, less toxic, and less cost for the final product.

The delivery platform described herein addresses current issues of nanocarriers on in vivo stability, biocompatibility, manufacturing scalability, tumor cell affinity and morphology (size and shape) tunability. In an aspect, the self-assembled discoidal PNA delivery vehicle has a stability of 3 months at 4° C. with no obvious visual change of appearance.

As used herein, PNA is a synthetic form of nucleic acids which lacks a net electrical charge along its protein-like backbone. Specifically, PNAs are molecules in which the phosphate backbone of an oligonucleotides is replaced in its entirety by repeating N-(2-aminoethyl)-glycine units and phosphodiester bonds are replaced by peptide bonds. The various heterocyclic bases are linked to the backbone by methylene carbonyl bonds. PNAs maintain spacing of heterocyclic bases that are similar to oligonucleotides but are achiral and neutrally charged molecules. PNAs are comprised of peptide nucleic acid monomers. The heterocyclic bases can be any of the standard bases (uracil, thymine, cytosine, adenine and guanine) or any of the modified heterocyclic bases described below.

PNAs can bind to DNA via Watson-Crick hydrogen bonds, but with binding affinities significantly higher than those of a corresponding nucleotide composed of DNA or RNA. The neutral backbone of PNAs decreases electrostatic repulsion between the PNA and target DNA phosphates. Under in vitro or in vivo conditions that promote opening of the duplex DNA, PNAs can mediate strand invasion of duplex DNA resulting in displacement of one DNA strand to form a D-loop.

As used herein, a bis-PNA is a PNA comprising two PNA molecules linked together by a linker of sufficient flexibility to form a single bis-PNA molecule. Exemplary linkers for bis-PNA molecules include, but are not limited to, 8-amino-3,6-dioxaoctanoic acid, referred to as an O-linker, and 6-aminohexanoic acid. Poly(ethylene) glycol monomers can also be used in bis-PNA linkers. A bis-PNA linker can contain multiple linker molecule monomers in any combination.

Tail clamp PNA (tcPNA) is a triplex-forming molecule including a "tail" added to the end of the Watson-Crick binding portion. Adding additional nucleobases, known as a "tail" or "tail clamp", to the Watson-Crick binding portion that bind to the target strand outside the triple helix further reduces the requirement for a polypurine:polypyrimidine stretch and increases the number of potential target sites. The tail is most typically added to the end of the Watson-Crick binding sequence furthest from the linker. This molecule therefore mediates a mode of binding to DNA that encompasses both triplex and duplex formation. For example, if the triplex-forming molecules are tail clamp PNA (tcPNA), the PNA/DNA/PNA triple helix portion and the PNA/DNA duplex portion both produce displacement of the pyrimidine-rich strand, creating an altered helical structure that strongly provokes the nucleotide excision repair pathway and activating the site for recombination with a donor DNA molecule.

Tails added to clamp PNAs (sometimes referred to as bis-PNAs) form tail-clamp PNAs are known to bind to DNA more efficiently due to low dissociation constants. The addition of the tail also increases binding specificity and binding stringency of the triplex-forming molecules to the target duplex. It has also been found that the addition of a tail to clamp PNA improves the frequency of recombination of the donor oligonucleotide at the target site compared to PNA without the tail.

PNAs can also include other positively charged moieties to increase the solubility of the PNA and increase the affinity of the PNA for duplex DNA. Commonly used positively charged moieties include the amino acids lysine and arginine, although other positively charged moieties may also be useful. Lysine and arginine residues can be added to a bis-PNA linker or can be added to the carboxy or the N-terminus of a PNA strand. Common modifications to PNA include, but are not limited to, incorporation of charged amino acid residues, such as lysine at the termini or in the interior part of the oligomer; inclusion of polar groups in the backbone, carboxymethylene bridge, and in the nucleobases; chiral PNAs bearing substituents on the original N-(2-aminoethyl)glycine backbone; replacement of the original aminoethylglycyl backbone skeleton with a negatively-charged scaffold; conjugation of high molecular weight polyethylene glycol (PEG) to one of the termini; fusion of PNA to DNA to generate a chimeric oligomer, redesign of the backbone architecture, conjugation of PNA to DNA or RNA. These modifications improve solubility but often result in reduced binding affinity and/or sequence specificity.

In an aspect, some or all of the PNA monomers are modified at the gamma position in the polyamide backbone (γPNAs) as illustrated below (wherein "B" is a nucleobase and "R" is a substitution at the gamma position).

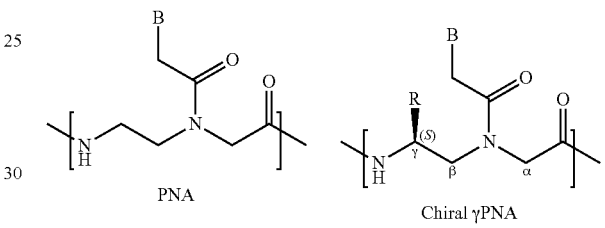

PNA

Chiral γPNA

Substitution at the gamma position creates chirality and provides helical pre-organization to the PNA oligomer, yielding substantially increased binding affinity to the target DNA. Other advantageous properties can be conferred depending on the chemical nature of the specific substitution at the gamma position (the "R" group in the chiral γPNA above). The synthesis of γPNAs is described in U.S. Pat. No. 10,221,216, incorporated herein by reference for the disclosure of γPNA and methods of synthesis of γPNA.

In some embodiments PNA-mediated gene editing are achieved via additional or alternative γ substitutions or other PNA chemical modifications including but limited to those introduced above and below. Examples of γ substitution with other side chains include that of alanine, serine, threonine, cysteine, valine, leucine, isoleucine, methionine, proline, phenylalanine, tyrosine, aspartic acid, glutamic acid, asparagine, glutamine, histidine, lysine, arginine, and the derivatives thereof. The "derivatives thereof" herein are defined as those chemical moieties that are covalently attached to these amino acid side chains, for instance, to that of serine, cysteine, threonine, tyrosine, aspartic acid, glutamic acid, asparagine, glutamine, lysine, and arginine.

In addition to γPNAs showing consistently improved gene editing potency, the level of off-target effects in the genome remains extremely low. This is in keeping with the lack of any intrinsic nuclease activity in the PNAs, and reflects the mechanism of triplex-induced gene editing, which acts by creating an altered helix at the target-binding site that engages endogenous high fidelity DNA repair pathways.

Additionally, PNAs can be modified to include guanidine-G-clamp ("G-clamp") PNA monomer(s) to enhance PNA binding. γPNAs with substitution of cytosine by clamp-G (9-(2-guanidinoethoxy) phenoxazine), a cytosine analog that can form five H-bonds with guanine, and can also provide extra base stacking due to the expanded phenoxazine ring system and substantially increased binding affinity. In vitro studies indicate that a single clamp-G substitution for C can substantially enhance the binding of a PNA-DNA duplex by 23° C. As a result, γPNAs containing G-clamp substitutions can have further increased activity.

The structure of a clamp-G monomer-to-G base pair (clamp-G indicated by the "X") is illustrated below in comparison to C-G base pair.

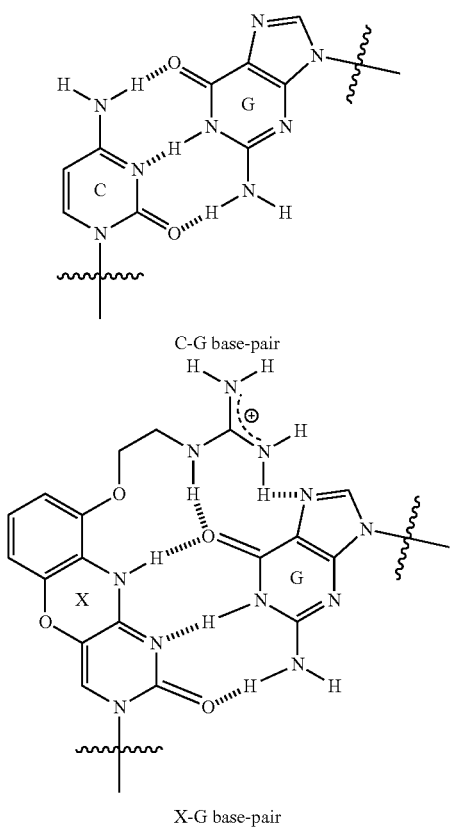

Triplex forming PNAs are described in U.S. Publication No. 2017/0283830, incorporated herein by reference for its disclosure of PNAs. Triplex-forming oligonucleotides (TFOs) are defined as oligonucleotides which bind as third strands to duplex DNA in a sequence specific manner. The oligonucleotides are synthetic or isolated nucleic acid molecules which selectively bind to or hybridize with a predetermined target sequence, target region, or target site within or adjacent to a human gene so as to form a triple-stranded structure.

In an aspect, the oligonucleotide is a single-stranded nucleic acid molecule between 7 and 40 nucleotides in length, most preferably 10 to 20 nucleotides in length for in vitro mutagenesis and 20 to 30 nucleotides in length for in vivo mutagenesis. The base composition may be homopurine or homopyrimidine. Alternatively, the base composition may be polypurine or polypyrimidine. However, other compositions are also useful.

The nucleotide sequence of the oligonucleotides is selected based on the sequence of the target sequence, the physical constraints imposed by the need to achieve binding of the oligonucleotide within the major groove of the target region, and the need to have a low dissociation constant ($K_d$) for the oligonucleotide/target sequence. The oligonucleotides have a base composition which is conducive to triple-helix formation and is generated based on one of the known structural motifs for third strand binding. The most stable complexes are formed on polypurine:polypyrimidine elements, which are relatively abundant in mammalian genomes. Triplex formation by TFOs can occur with the third strand oriented either parallel or anti-parallel to the purine strand of the duplex. In the anti-parallel, purine motif, the triplets are G.G:C and A.A:T, whereas in the parallel pyrimidine motif, the canonical triplets are C$^+$.G:C and T.A:T. The triplex structures are stabilized by two Hoogsteen hydrogen bonds between the bases in the TFO strand and the purine strand in the duplex. A review of base compositions for third strand binding oligonucleotides is provided in U.S. Pat. No. 5,422,251.

In an aspect the oligonucleotide binds to or hybridizes to the target sequence under conditions of high stringency and specificity. Most preferably, the oligonucleotides bind in a sequence-specific manner within the major groove of duplex DNA. Reaction conditions for in vitro triple helix formation of an oligonucleotide probe or primer to a nucleic acid sequence vary from oligonucleotide to oligonucleotide, depending on factors such as oligonucleotide length, the number of G:C and A:T base pairs, and the composition of the buffer utilized in the hybridization reaction. An oligonucleotide substantially complementary, based on the third strand binding code, to the target region of the double-stranded nucleic acid molecule is preferred.

Mini-Peg-containing γ-PNAs are described in U.S. Pat. No. 10,793,605, incorporated herein by reference for its disclosure of mini-PEG γ-PNAs and their methods of synthesis. Mini-Peg-containing γ-PNAs include a monomer comprising a PNA monomer of formula I:

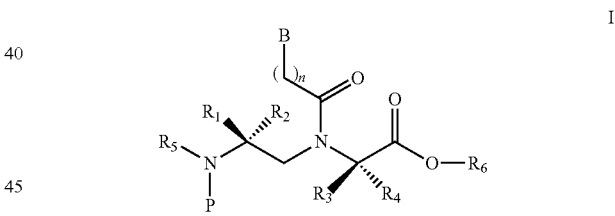

In Formula I, B is a nucleic acid base selected from adenine, guanine, cytosine, thymine or uracil. Substituent groups $R_1$, $R_2$ and $R_5$ each independently are selected from the group consisting of H, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, —CH$_2$(OCH$_2$—CH$_2$)$_q$OP1, —CH$_2$(OCH$_2$—CH$_2$)$_q$—NHP$_1$, —CH$_2$—(OCH$_2$—CH$_2$—O)$_q$—SP$_1$ and —CH$_2$—(SCH$_2$—CH$_2$)$_q$—SP$_1$.

Substituents $R_3$ and $R_4$ each independently are H while $R_6$ is selected from the group consisting of H, linear or branched ($C_1$-$C_8$)alkyl, substituted or unsubstituted ($C_3$-$C_8$) aryl and ($C_3$-$C_8$)aryl($C_1$-$C_6$)alkylene.

According to Formula I, P is selected from the group consisting of H, 9-fluorenylmethyloxy carbonyl, Boc, benzyloxycarbonyl, tosylate, benzyl, alloc, trityl, dimethoxytrityl and monomethoxytrityl and substituent $P_1$ is selected from the group consisting of H, ($C_1$-$C_8$)alkyl, ($C_2$-$C_8$) alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene. Subscripts n and q are each independently integers between 0 and 10 inclusive.

According to one embodiment, each of $R_1$ and $R_2$ in a Formula I compound is independently —$CH_2$—O—($CH_2$—$CH_2$—O)$_q P_1$. For some Formula I compounds each of $R_1$ is $CH_2$—(O—$CH_2$—$CH_2$—)$_n OP_1$ and $R_2$ is selected from the group consisting of H, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, —$CH_2$—(O$CH_2$—$CH_2$)$_q$—NHP1, —$CH_2$—(O$CH_2$—$CH_2$—O)$_q$—$SP_1$ and —$CH_2$—($SCH_2$—$CH_2$)$_q$—$SP_1$. For certain Formula I compounds $R_1$ is —$CH_2$—(O—$CH_2$—$CH_2$—))$_q OP_1$, $R_2$ is H and substituent $P_1$ is H or ($C_1$-$C_8$)alkyl.

In an aspect, a Mini-Peg-containing γ-PNAs include a monomer comprising a PNA monomer of formula I, wherein
B is adenine, guanine, cytosine, thymine, or uracil;
P is selected from the group consisting of hydrogen (H), 9-fluorenylmethyloxycarbonyl (Fmoc), t-butyloxycarbonyl (Boc), benzyloxycarbonyl (Cbz), benzyl (Bn), tosylate (Tos), allyloxycarbonyl (alloc), benzhydryloxycarbonyl (Bhoc), trityl (Trt), monomethoxytrityl (MMT) and dimethoxytrityl (DMT);
each of $R_1$ and $R_2$ is independently selected from the group consisting of hydrogen (H), linear or branched ($C_1$-$C_8$)alkyl, ($C_2$-$C_8$)alkenyl, ($C_2$-$C_8$)alkynyl, ($C_1$-$C_8$) hydroxylalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, and

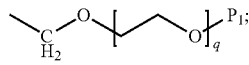

provided that at least one of $R_1$ and $R_2$ is

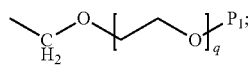

each of $R_3$ and $R_4$ is independently selected from the group consisting of hydrogen (H) and

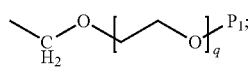

$R_5$ is selected from the group consisting of hydrogen (H), linear or branched ($C_1$-$C_8$)alkyl, ($C_2$-$C_8$)alkenyl, ($C_2$-$C_8$)alkynyl, ($C_1$-$C_8$)hydroxylalkyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene;
$R_6$ is selected from the group consisting of hydrogen (H), linear or branched ($C_1$-$C_8$)alkyl, substituted or unsubstituted ($C_3$-$C_8$)aryl and ($C_3$-$C_8$)aryl($C_1$-$C_6$)alkylene;
$P_1$ is selected from the group consisting of hydrogen (H), linear or branched ($C_1$-$C_8$)alkyl, 9-fluorenylmethyloxycarbonyl (Fmoc), t-butyloxycarbonyl (Boc), benzyloxycarbonyl (Cbz), benzyl (Bn), tosylate (Tos), allyloxycarbonyl (alloc), trityl (Trt), monomethoxytrityl (MMT) and dimethoxytrityl (DMT);
n is an integer from 0 to 10, inclusive; and
q is an integer from 1 to 10, inclusive.

Formula I compounds are chiral. The stereochemical purity of a Formula I compound is in the range from about 80% to about 99% at the Cγ-position. In one embodiment the stereochemical purity is at least 90% at the Cγ-position. According to yet another embodiment the stereochemical purity of a Formula I compound is at least 99% at the Cγ-position.

PNAs optionally include other positively charged moieties to increase the solubility of the PNA and increase the affinity of the PNA for duplex DNA. Commonly used positively charged moieties include the amino acids lysine and arginine, although other positively charged moieties may also be useful. Lysine and arginine residues can be added to a bis-PNA linker or can be added to the carboxy or the N-terminus of a PNA strand.

The oligonucleotides can be generated using known DNA synthesis procedures. In one embodiment, oligonucleotides are generated synthetically. Oligonucleotides can also be chemically modified using standard methods that are well known in the art.

In an aspect, a one pot method of self assembling a discoidal PNA delivery vehicle comprising encapsulated PNA comprises mixing a cosolvent; a zwitterionic short chain 5:0 to 7:0 diacyl lipid comprising a phosphatidylcholine or phosphatidylethanolamine hydrophilic headgroup; a zwitterionic long chain 14:0 to 18:0 diacyl lipid comprising a phosphatidylcholine or phosphatidylethanolamine hydrophilic headgroup; a charged long chain 12:0 to 18:0 diacyl lipid comprising a phosphatidylglycerol, phosphoinositol, phosphatidic acid, or phosphatidylserine hydrophilic headgroup; a PEGylated lipid of the formula distearoyl phosphoethanolamine (DSPE)-PEG$_n$-TG, wherein n is the molecular weight of the PEG and is 1000 to 5000, and TG is a terminal group which is hydroxyl, succinyl, cyanur, folate, maleimide, pyridoxal-5'-diphosphate (PDP), amine, biotin, trimethylsilyl (TMS), carboxylic acid, azide, dibenzocyclooctyne (DBCO), or benzylguanine; and the PNA molecule; providing sufficient time for the discoidal PNA delivery vehicle to self assemble and encapsulate the PNA; and optionally removing the cosolvent. In specific aspect, the molar ratio of the zwitterionic long chain diacyl lipid and the charged long chain diacyl lipid to the short chain diacyl lipid is 0.5 to 5, the molar ratio of the charged long chain diacyl lipid to the zwitterionic long chain diacyl lipid is greater than 0.01, the molar % of the PEGylated lipid to all lipids is 1% to 5%, and the ratio of PNA to total lipid is 1:500 to 1:2500.

In an aspect, the co-dissolution time is <10 minutes, the cosolvent evaporation time is <3 hours and the time for self-assembly in aqueous solution is <1 hours. The time is practically independent of the quantity to be prepared.

As defined herein, a cosolvent is a solvent for both lipids and PNA. Exemplary cosolvents include DMF and DMSO.

In an aspect, the encapsulation efficiency of the PNA is >90%.

In another aspect, a method of enhancing cellular uptake of PNA comprises contacting a cell with the self assembling discoidal PNA delivery vehicle described herein, wherein the self assembling a discoidal PNA delivery vehicle provides improved cellular uptake compared to a liposome. In an aspect, the cellular uptake of nanodiscs is at least 5 times higher than that of vesicles made of the same chemical composition.

In an aspect, the PNA modifies the expression of a gene in the cell. By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional promoter and other cis-acting elements, such as response elements and/or enhancers; an expressed sequence that typically encodes a protein (open-reading frame or ORF) or functional/structural RNA, and a polyadenylation sequence), to produce a gene product (typically a protein, optionally post-translationally modified or a functional/structural RNA). By "expression of genes under transcriptional control of," or alternately "subject to control by," a designated sequence, it is meant gene expression from a gene containing the designated sequence operably linked (functionally attached, typically in cis) to the gene. The designated sequence may be all or part of the transcriptional elements (without limitation, promoters, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when an amount of the respective inducer is administered to the expression system (e.g., cell) effective to cause expression of the gene.

As used herein, the term "knockdown" means that expression of one or more genes in an organism is reduced, typically significantly, with respect to a functional gene, such as to a therapeutically effective degree. Gene knockdown also includes complete gene silencing. As used herein, "gene silencing" means that expression of a gene is essentially completely prevented. Knockdown and gene silencing may occur either at the transcriptional stage or the translational stage. Use of the described recognition modules, e.g., γPNA precursors, to target an RNA in a cell, such as an mRNA, will modify gene expression, by knocking down or silencing a gene or genes at the translational stage.

The self-assembled discoidal PNA delivery vehicles described herein can be used in the treatment of genetic diseases such as those characterized by unstable repeats such as Huntington's disease. PNAs can be used in the treatment of cancer (telomere), bacterial infection (resistant strains, targeting the repeated and conserved elements unique to the pathogenic strains), parasite infection such as malaria (targeting microsatellites that have been shown to be essential in the replication and life cycle of the plasmodium), and viral infection such as hepatitis C (affecting 3% of the world population for which there are no effective treatment by targeting the repeated elements within the viral RNA genome), and AIDS (this is a rapidly moving target for which the new mutant sequence can be chased after by dialing-in the corresponding nucleobase sequence in the recognition modules).

Advantageously, the cellular uptake of the self-assembled discoidal PNA delivery vehicles comprises minimal trapping in endosomes as noticed by uniform distribution in the cytoplasm rather than puncta structures.

The invention is further illustrated by the following non-limiting examples.

EXAMPLES

Methods

Materials: The zwitterionic short-chain dihexanoyl phosphatidylcholine (di-6:0, DHPC) lipid, and zwitterionic long-chain dipalmitoyl phosphatidylcholine (di-16:0, DPPC) lipid, negatively charged long-chain dipalmitoyl phosphatidylglycerol (DPPG), 1,2-dipalmitoyl-3-trimethylammonium-propane (chloride salt) (DOTAP), and polyethylene glycol (PEG2000)-conjugated distearoyl phosphoethanolamine (DSPE-PEG2000) were purchased from Avanti Polar Lipids (Alabaster, AL, USA). They are used without further purification. Phosphate buffered saline (PBS) powder was purchased from Sigma-Aldrich (St. Louis, MO). Dulbecco's Phosphate-Buffered Saline (DPBS) was purchased from Life Technologies (Grand Island, NY, USA). Boc-protected PNA monomers used for PNA synthesis were purchased from ASM Chemicals and Research (Hanover, Germany). Boc-MiniPEG and Nα-t-Butyloxycarbonyl-Nγ-Benzyloxycarbonyl-L-Lysine (Boc-Lys(Z)-OH) were purchased from Peptides International (Kentucky, USA). Boc-5-carboxytetramethylrhodamine (TAMRA) dye was purchased from VWR (Radnor, Pennsylvania).

Chlorpromazine, Amiloride and Genistein were purchased from Sigma-Aldrich (MO, USA). Human embryonic kidney (HEK) cells (ATCC® CRL-1573™) were purchased from ATCC (Virginia, USA). CellTiter 96® Aqueous One Solution Cell Proliferation Assay (MTS) was purchased from Promega (WI, USA).

Synthesis of folate conjugated Lipid NPs of different shapes: DPPC, DHPC, and DSPE-PEG2000, as well as either negatively charged DPPG or positively charged DOTAP were used for NPs preparation. The mixture, DPPC/DHPC/DPPG/DSPE-PEG2000 was prepared at a molar ratio of 69.58/25.1/3.76/2.0. All lipid molecules of the required weights were first homogenized in chloroform. After the removal of the solvent by a vacuum oven, the dried samples were then re-dispersed in filtered deionized (DI) water to make stock suspensions with a total lipid weight concentration, $C_{lp}$, of 10% (wt). After successive vortexing and temperature cycling between 25° C. and 70° C., the stock dispersions were then progressively diluted at room temperature to $C_{lp}$=1.0 mg/ml with PBS solution.

The PNA-entrapped NDs were prepared at PNA:lipid molar ratios of 1:200, 1:500, 1:1000 and 1:2500, homogeneously dispersed in chloroform. After being dried, the sample was re-hydrated in water to form a 10 wt. % mother solution by a proper temperature cycling and vortexing. The solution was then centrifuged at 10,000 rpm for 10 minutes in a Beckman Counter centrifuge to separate the aggregates and large particles and diluted to the desired concentration prior to the use for studies.

Measure the loading of nucleic acids in NDs: In order to investigate the encapsulation efficiencies of the PNAs, aqueous solutions of the ND encapsulated PNAs were diluted to 0.1 wt. % lipid concentration and centrifuged at 10000 rpm for 15 minutes. The top supernatant was separated as the encapsulated portion. The precipitates also were used to confirm the amount of non-encapsulated PNAs. Both supernatants and precipitations were dried under nitrogen gas and redispersed accordingly with DMSO. After separating the precipitation and supernatant, the UV-visible absorption spectra (190-800 nm) of all samples were recorded by a Cary 5000 UV-Vis-NIR spectrometer (Agilent, USA). The absorbance of lipid compositions and PNA molecules alone were also used for the pre-calibrated curves and extinction coefficient confirmation. The encapsulation efficiencies (EE) of encapsulated PNAs in each sample was measured via the equation below:

$$EE = \frac{[(OD \times Mw \times \text{dilution factor})/\varepsilon]}{\text{Initial Concentration}} \times 100,$$

where OD, Mw, $\varepsilon$ are optical density (normalized absorbance intensity) and molecular weight of the PNA, extinction coefficient, respectively, dilution factor is 1000, and Initial concentration is in the unit of 0.01 wt. % of lipid nanocarrier.

Small angle X-ray scattering (SAXS): SAXS measurements were conducted at 161D-LiX Beamline at National Synchrotron Light Source II located at the Brookhaven National Laboratory (Upton, NY), using the standard flow-cell-based solution scattering setup with the X-ray energy of 13.5 keV. The SAXS intensity is expressed as a function of the scattering vector, $$q(q \equiv \frac{4\pi}{\lambda} \sin\frac{\theta}{2},$$

where $\theta$ is the scattering angle) varies from 0.005 to 2.5 Å$^{-1}$. Radial averaging and q-conversion of data were performed using the standard software merging data from all three detectors used in the measurements. The transmission correction and background subtraction were performed to minimize the intensity of the hydrogen bond from water at approximately 2.0 Å$^{-1}$.

Dynamic light scattering (DLS): Size and population distribution of pristine and PNA-encapsulated nanodiscs were also determined by ALV/CGS-8F/4 (ALV compact system, Germany) instrument at a 632.8 nm laser beam. The samples were dissolved and homogenized in filtered DI water to 0.1 wt %. The results were reported as the average of 10 measurements.

Transmission electron microscopy (TEM): Negatively-stained transmission electron microscopic (TEM) images were obtained using FEI Tecnai T12. The samples were prepared by spreading 5 μL 0.001 wt. % solution on a 400 mesh Formvar/carbon film copper grid (Electron Microscopy Sciences, PA, USA) and negative staining was applied with 10 mg/mL of Uranyl acetate (SPI Supplies, PA, USA). The grids were then dried at 25° C. The accelerating voltage of the TEM was set at 80 kV.

Calculation of molecular lipophilic surface potential (MLSP): MLSP describes the 3-D lipophilic influence of all fragments of a molecule and can be calculated at given points in space. MLSP analysis of the PNA 155-TAMRA and PNA 210-TAMRA molecules were carried out using the Molinspiration Property Calculation Service molecular modeling package in order to study the feasibility of encapsulation of them inside the lipid bilayers of nanodiscs. The Gasteiger-Mickel charges were assigned to the atoms of TMS structure, and surfaces were generated. The color ramp for the MLSP ranges from violet/blue color representing the higher lipophilic potential (LP) to the red color representing the lower LP.

AntimiR-PNA based oligomers: PNA-155 and PNA-210 were synthesized via solid phase synthesis using MBHA (4-Methylbenzhydrylamine) resin and Boc-monomers (A, T, C, G). TAMRA dye was conjugated to N-terminus of PNAs with Boc-miniPEG-3 linker (ooo). PNAs were then cleaved from the resin using cleavage cocktail containing m-cresol:thioanisole:trifluoromethanesulfonic acid (TFMSA):trifluoroacetic acid (TFA) (1:1:2:4) followed by precipitation using diethyl ether. PNAs were purified and characterized using reverse-phase high-performance liquid chromatography (HPLC) and matrix-assisted laser desorption/ionization-time of flight (MALDI-TOF) spectroscopy respectively. The concentration of PNAs was determined using UV-vis spectroscopy, and extinction coefficient of PNAs was calculated using extinction coefficient of individual monomers (13,700 M$^{-1}$cm$^{-1}$ (A), 6,600 M$^{-1}$cm$^{-1}$ (C), 11,700 M$^{-1}$cm$^{-1}$ (G), and 8,600 M$^{-1}$cm$^{-1}$ (T)) of the sequence.

PNA-155-TAMRA:
(SEQ ID NO: 1)
5' TAMRA-ooo-ACCCCTATCACGATTAGCATTAA-Lys 3'

PNA-210-TAMRA:
(SEQ ID NO: 2)
5' TAMRA-ooo-TCAGCCGCTGTCACACGCACAG-Lys-3'

Confocal microscopy: Approximately 100,000 HeLa cells (ATCC® CCL-2™) were allowed to seed overnight on coverslips in 12 well plates. Cells were treated with only PNA-155-TAMRA, and PNA-155-TAMRA or PNA-210-TAMRA entrapped in optimized nanodiscs (1:2500(−)) overnight. Amount of PNA-155-TAMRA used was kept at the same level as PNA-155-TAMRA entrapped in NDs. After 24 hours, cells were gently washed with 1 mL phosphate buffered saline (PBS) (4×) at room temperature (RT). Further, the cells were fixed by adding 1 mL of 4% paraformaldehyde at 37° C. for 10 minutes. After washing the cells with 1 mL, PBS (2×), cells were permeabilized using 1 mL of 0.1% Triton™-X in PBS at 37° C. for 10 minutes. Cells were mounted on a slide using ProLong™ Diamond Antifade Mountant with DAPI (Life Technologies, Carlsbad, CA, USA). Samples were allowed to harden at 4° C. overnight and images were taken using a Nikon A1R spectral confocal microscope.

Flow cytometry analysis: Approximately 100,000 HeLa cells (ATCC® CCL-2™) were seeded in 12 well plates overnight followed by treatment with PNA-210-TAMRA or PNA-155-TAMRA containing nanodiscs for 2.4 hours. Cells were then washed with PBS (4×), and trypsinization was done using 0.25% trypsin-EDTA (Gibco®, Life Technologies) at 37° C. for 4 minutes. Trypsinized cells were suspended in 1 mL of DMEM, 10% FBS media and centrifuged at 1000 RPM for 4 minutes at 4° C. Further, the cells were washed twice with 1 mL of PBS at 1000 RPM for 4 minutes at 4° C. Fixation of cells was done using 300 μL of 4% paraformaldehyde and flow cytometry was done using LSR Fortessa™ X-20 Cell Analyzer (BD Biosciences, San Jose, CA). Results obtained were analyzed using FlowJo analysis software.

Real-time PCR studies: RNA was extracted from HeLa cells (ATCC® CCL-2™) treated with PNA-155-TAMRA and nanodiscs containing PNA-155-TAMRA using RNeasy® Mini Kit (Qiagen, Hilden, Germany). TaqMan™ MicroRNA Assay (Assay ID: 467534_mat) (Applied Biosystem, Foster City, CA) was used to measure miR-155 levels. cDNA was synthesized using miR-155 reverse transcriptase (RT) primers (TaqMan™ MicroRNA Assay), 10×RT buffer, 100 mM dNTPs in the presence of RNase inhibitor (Applied Biosystem, Foster City, CA). Reverse transcription was done under the conditions (16° C. for 30 minutes, 42° C. for 30 minutes, 85° C. for 5 minutes) provided with TaqMan™ MicroRNA Assay using the thermal cycler (T100™, Bio-Rad, Hercules, CA).

MiR-155 specific primers (TaqMan™ MicroRNA Assay) and TaqMan™ Universal Master Mix II, with UNG (Applied Biosystem, Foster City, CA) were used under the conditions specified in the assay (50° C. for 2 minutes, 95° C. for 10 minutes, (95° C. for 15 seconds, 60° C. for 60 seconds)×40 cycles) for amplification of cDNA. U6 snRNA (TaqMan™ microRNA Control) assay was used as a control. No template control was used for both the U6 snRNA and miR-155 expression levels.

Endocytosis inhibitor Study: HeLa cells were incubated with chlorpromazine (10 μg/mL), amiloride (10 mM) and genistein (200 μmol/l) at 37° C. After 30 minutes, cells were treated with PNA-155-TAMRA NDs at a dose of 4 μM/ml for one hour at 37° C. Cells were washed with PBS and fixed using 4% paraformaldehyde followed with analysis by LSR Fortessa™ X-20 Cell Analyzer (BD Biosciences, San Jose, CA). For confocal microscopy, cells pre-treated with endocytosis inhibitors for 30 minutes, were incubated with PNA-155-TAMRA NDs for one hour. After washing and fixing with 4% paraformaldehyde, cells were mounted in ProLong™ Diamond Antifade Mountant with DAPI (Life Technologies, Carlsbad, CA, USA). Images were taken by Nikon AIR spectral confocal microscope.

Safety study in primary cells: HEK293 cells (2000 cells/well) were seeded overnight in 96 well plates. Cells were treated with PNA-155-TAMRA NDs (4 μM/ml) and incubated at 37° C. After 24 hours, cells were washed with PBS and incubated in fresh culture medium with 20 μl of MTS reagent (CellTiter 96® Aqueous One Solution Cell Proliferation Assay) at 37° C. After an hour, absorbance was measured at 490 nm and used to calculate % cell viability.

Western blot analysis: HeLa cells were treated with NDs and protein was extracted with Radio-Immunoprecipitation Assay lysis buffer. Total protein of 50-100 mg was run on SDS/polyacrylamide gel electrophoresis gels and transferred to nitrocellulose membranes. Antibodies used were: Anti-p53 Antibody (DO-1) (SCBT—Santa Cruz Biotechnology, sc-126) at 1:500 and Anti-β-Actin antibody (Sigma, A5316) at 1:10,000.

Example 1: Lipid-Based Bicellar Formulations and Characterization

Positively and negatively charged NDs were prepared to evaluate their antimiR PNA payload properties. In parallel, three formulations comprising different PNA:lipid molar ratio; 1:2500, 1:1000 and 1:200 were compared. NDs were formulated based on established protocols. We did not notice any significant decreases in reaction yield during NDs formulation process containing antimiR PNAs.

Figure 2A:
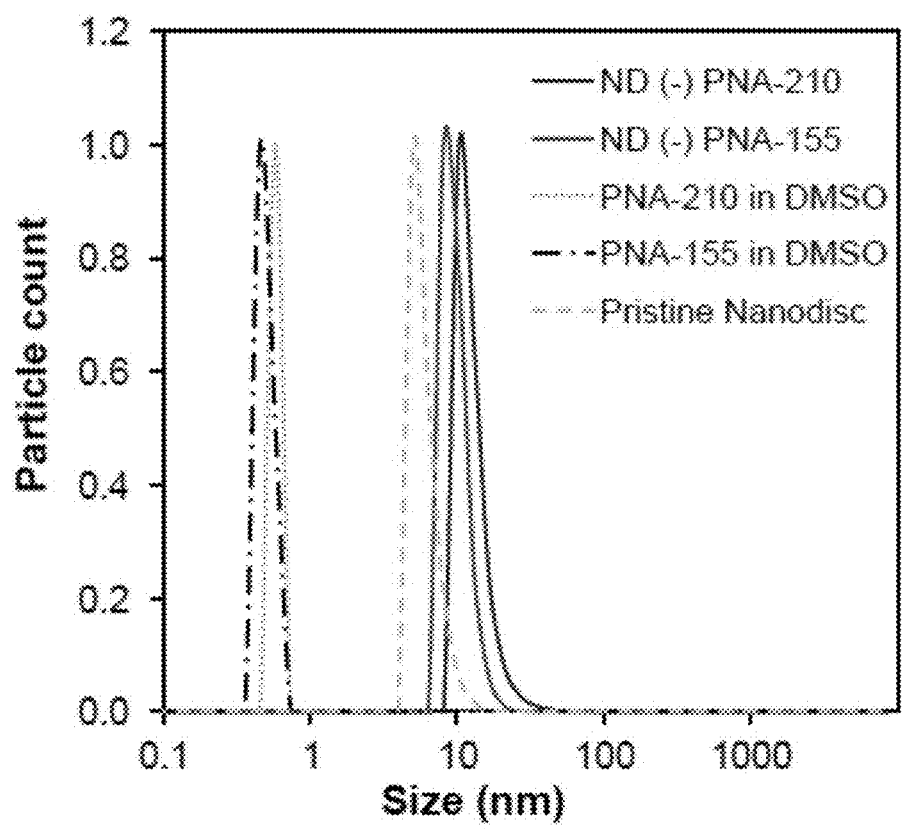
FIGS. 2A-C show size distribution and images of nanodiscs. (A) Size distribution of nanodiscs (ND) and nanovesicles in the presence (solid) and absence (dotted) folate ligand. The hydrodynamic radius, $R_H$ of NPs was 10 to approximately 12 nm for ND, consistent with the best fitting dimensions from SAXS data. (B and C) TEM images of negative charge ND (−) and positive charge ND (+) containing lipid:PNA molar ratio of 1:2500 loaded with PNA-210. The planar and rim views are pointed by yellow and green arrows, respectively. The radius of NPs was 10 to approximately 12 nm for ND, consistent with the best fitting dimensions from DLS data.

The distribution of hydrodynamic radii ($R_H$) of antimiRs loaded and pristine NDs was measured using a dynamic light scattering (DLS) method. In the pristine NDs, a radius of approximately 8.5 nm was observed that is consistent with the literature. However, an increase in $R_H$ was noted for antimiR PNA loaded negatively-charged NDs regardless of their surface charge (FIG. 2A). For the samples with PNA: lipid molar ratios of 1:2500 and 1:1000, the RHs remain less than approximately 15 nm with a uniform distribution (data not shown), while as the PNA:lipid molar ratio reaches 1:100, the $R_H$ increases significantly with a broader distribution, implicative of PNA-induced irregularity. Further, the results showed similar size and uniformity for both PNAs, i.e., antimiR PNA-155 and PNA-210, at corresponding compositions, implying that the negatively-charged ND is capable of encapsulating the antimiR regardless of their nucleobase sequence composition. In contrast to the negatively charged NDs, the positively charged NDs result in large aggregates even at PNA:lipid ratios of 1:1000 and 1:2500, unlikely to fully retain the nanodiscoidal shape. Without being held to theory, it is believed that the electrostatic interaction between positive charge of bicelles and negative charge of PNA nucleobase interfered with the bicellar self-assembly.

Figure 2B:
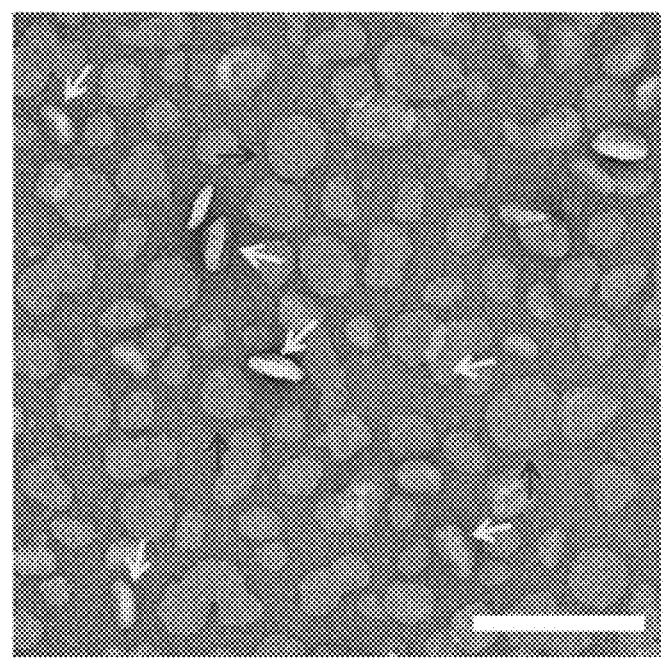
Figure 2C:
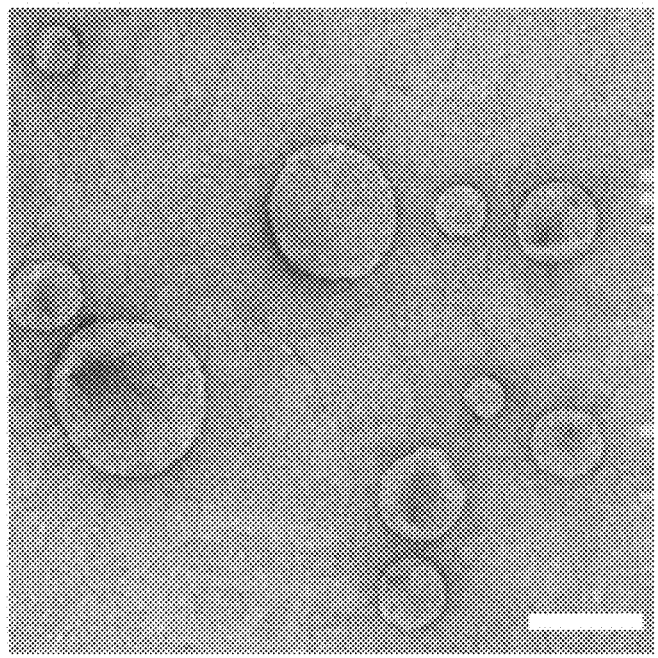

Further, the morphologies of lipid/PNA complexes were examined by transmission electron microscopy (TEM). The TEM and AFM images (FIG. 2B and data not shown) indicate uniform discoidal morphology for both PNA-210 and PNA-155 (PNA:lipid=1:2500), respectively, as encapsulated in the negatively charged bicelles. The fact that no noticeable difference in shape and size is found for both systems agrees well with the prior DLS results. Nevertheless, antimiR PNA-210 loaded in positively-charged bicelles results in large vesicles (FIG. 2C), also consistent with the DLS data.

Example 2: Encapsulation Efficiency

Incorporating hydrophobic small molecules trapped in the lipid bilayer of liposomes or biomimetic membranes has been investigated experimental and theoretically. The encapsulation efficiencies for hydrophobic molecules in liposomes are generally not high; however, it has been reported that the bilayer defects induced by the short-chain lipids enhance the activity of membrane to host lipophilic molecules. It is expected that the encapsulation efficiency of hydrophobic molecules in NDs is higher than in liposomes. Due to the low solubility of PNAs in water, centrifugation is applied to the PNA-loaded NDs to remove non-encapsulated PNA aggregates. In contrast to the colorless pristine ND solution, the PNA-encapsulated supernatants are pinkish depending on the concentration of encapsulated PNA. The entrapped amount of PNAs can be obtained from the UV-vis absorption spectra compared against a pre-calibrated UV-vis absorption spectrum, whose intensity is linearly dependent on the concentration of PNA (data not shown).

Figure 3:
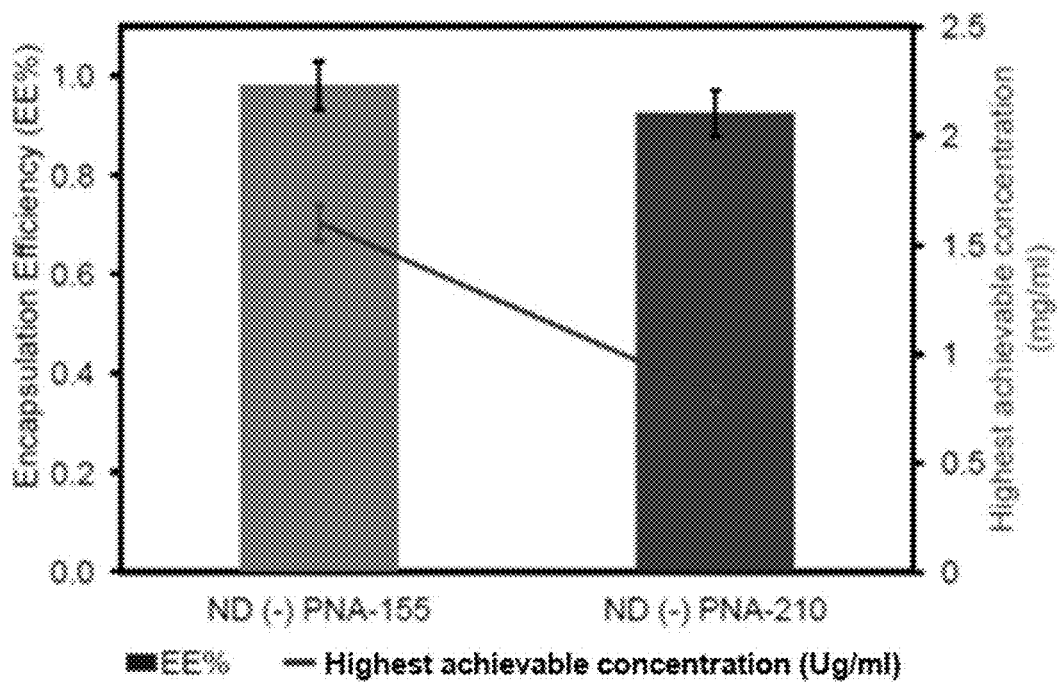
FIG. 3 shows encapsulation efficiencies (EE) of antimiR-155 and 210 PNAs in negative charge containing NDs. The bar chart shows the encapsulation rates calculated by the ratio of encapsulated PNA molecules compared to the initial mass of PNA added. The line chart (right y-axis) indicates the highest achievable concentration of the PNAs encapsulated in NDs and stable in the aqueous phase.

The encapsulation efficiencies (EE) of AntimiR PNA-210 and 155 encapsulated in NDs are similar to each other at low PNA:lipid ratios (FIG. 3). However, with increased PNA: lipid ratio, the encapsulation efficiency decreased drastically (data not shown). For instance, for a PNA:lipid ratio of 1:100, the EE is less than 10%, while with lower ratios, 1:1000 and 1:2500 the encapsulation rates in NDs are 95±4 and 92±3, respectively (data not shown). This further confirms that the lipophilicity of PNA allows for its interaction with bicelle, thus forming stable nanocomplex, and overwhelming insoluble PNA can be separated from the system through centrifugation. The fact that the centrifugation speed does not affect the experimental outcome of encapsulation efficiency indicates that the current centrifugation speed and time is sufficient to separate the encapsulated and unencapsulated PNAs.

Figure 4:
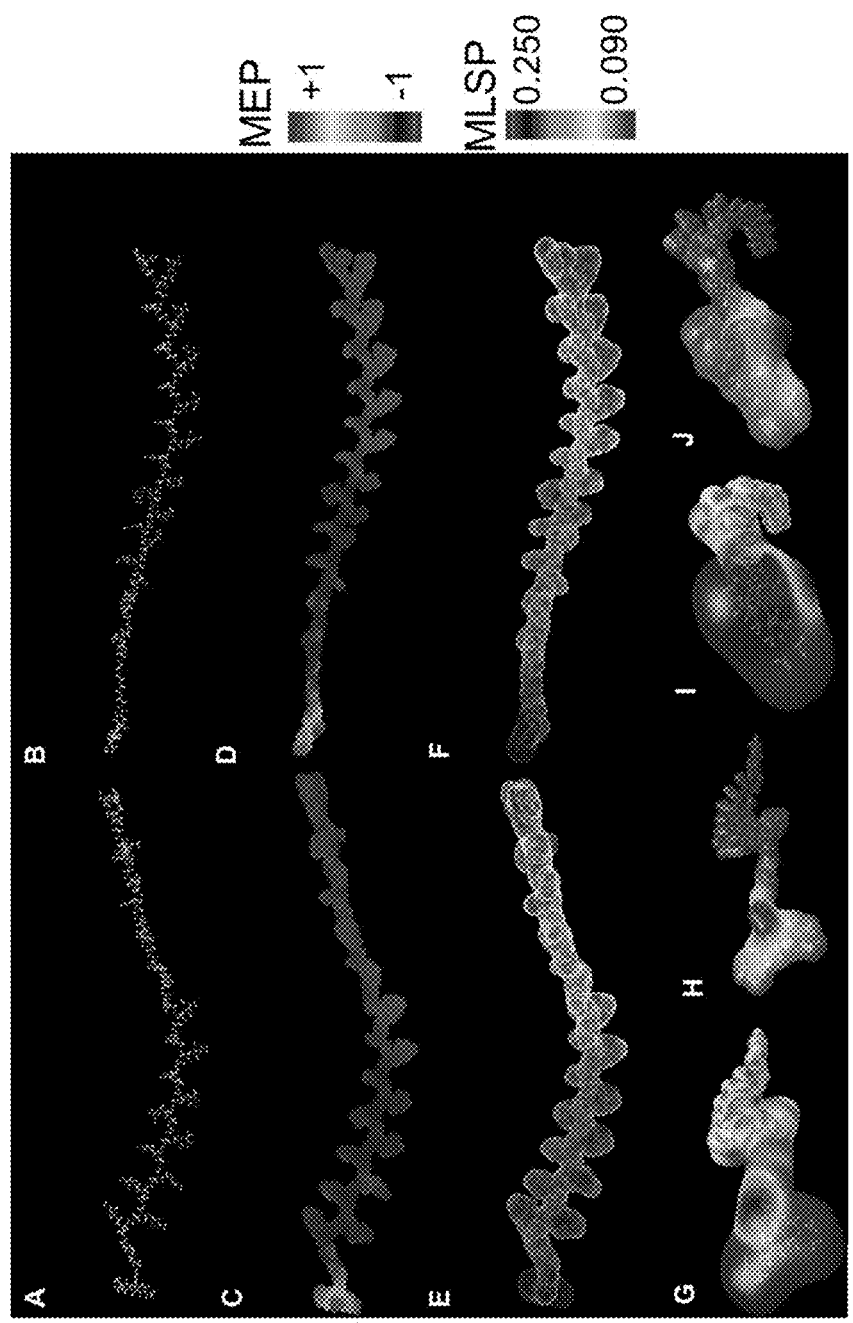
FIGS. 4A-J show simulation studies for the antimiR PNA molecules, using VEGAZZ® software. (A and B) Chemical structure of antimiR PNA-155 and 210. TAMRA is at the far-left side of the structure. (C and D) Molecular electrostatic potential (MEP) of PNA-155 and 210. (E and F) MLSP analysis of PNA-155 and PNA 210. Moving from blue to red on the scale indicates increasing MLSP. Encircled red portions show lipophilic regions exposed on the surface of the molecules, which provides an ideal segment in the molecule to be incorporated into the lipid bilayer. Both PNA molecules show low lipophilicity and low hydrophilicity in the main backbone, while the TAMRA part is a highly lipophilic structure. (G and I) A higher magnification of the TAMRA domains of AntimiR PNA molecules is also provided in parts. (H and J) indicate the multiple hydrophilic and hydrophobic domains of PNA backbone respectively.

Example 3: Molecular Modeling Analysis of ANTIMIR PNA Sequences and SAXS Analysis The encapsulation mechanism of antimiR PNAs in NDs can be understood through the analysis by the Molecular Lipophilicity Surface Potential (MLSP) and Molecular electrostatic potential (MEP) based methods (FIG. 4), which were performed using VEGAZZ software. The analysis shows that TAMRA at the N-terminus of PNAs are more lipophilic and therefore can interact with the hydrophobic portion of the NDs. However, PNA backbone contains scattered hydrophilic domains, which could be exposed to the aqueous environment outside of the NDs. The following SAXS analysis will provide some insight into the location of PNA in NDs.

parison between the best fit of pristine ND and PNA-loaded SAXS data (individual plots at the bottom of FIG. 5) shows significant differences. The general conclusion of the best fitting procedure indicates the encapsulation of the antimiR-PNAs has no significant structural disturbance on the discoidal geometry, while some variation in the dimensions of the ND is found and will be discussed below.

TABLE 1

THE BEST-FITTING PARAMETERS OBTAINED FROM THE SAXS DATA OF THE NDS

Core-Shell Discoidal Model
(with invariant $t_{shell} = 14.9$ Å, and $\square_w = 9.40 \times 10^{-6}$ Å$^{-2}$)

| | $\rho_{shell}$, × $10^{-6}$ Å$^{-2}$ | $\rho_{rim}$, × $10^{-6}$ Å$^{-2}$ | $t_{rim}$, × Å | $\rho_{core}$, × $10^{-6}$ Å$^{-2}$ | $t_{core}$, Å | $R_{core}$, Å | Disc Diameter, Å |
|---|---|---|---|---|---|---|---|
| NDs | 10.7 (±0.1) | 9.8 (±0.1) | 27.1 (±0.5) | 7.1 (±01.1) | 25.1 (±0.2) | 95 (±8) | 244 (±9) |
| ND(-)PNA 210 1:500 | 12.9 (±0.9) | 9.9 (±0.6) | 52.5 (±4.5) | 7.1 (±2.2) | 24.4 (±0.3) | 148 (±11) | 400 (±16) |
| ND (-)PNA 210 1:2500 | 12.6 (±0.4) | 9.9 (±1.5) | 47.8 (±2.9) | 6.75 (±1.2) | 24.8 (±0.7) | 106 (±1) | 308 (±4) |
| ND (-) PNA155 1:2500 | 10.7 (±1.7) | 9.7 (±3.5) | 51.8 (±2.8) | 8.3 (±0.8) | 24.6 (±0.6) | 135 (±2) | 375 (±5) |

Figure 5:
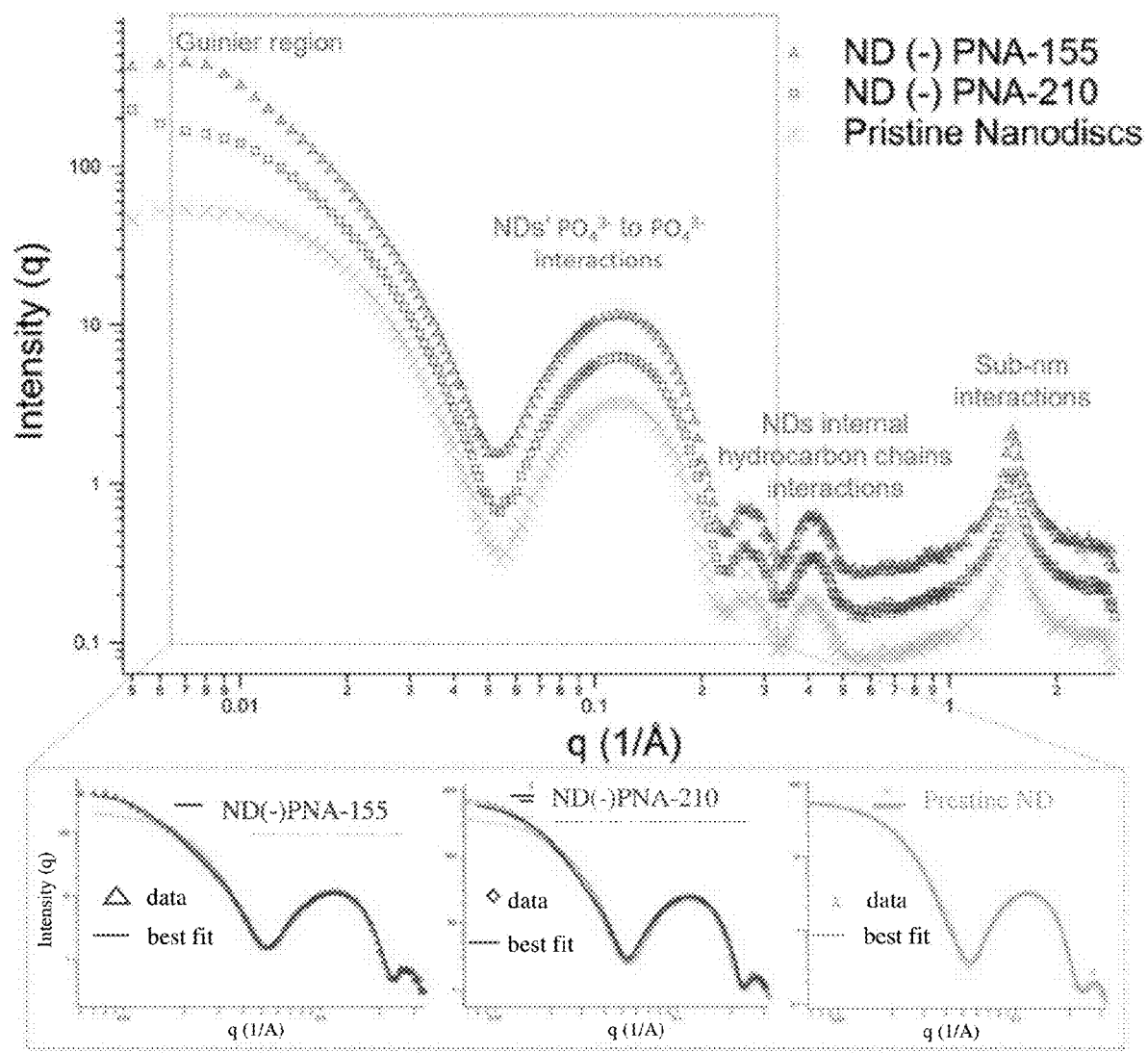
FIG. 5 shows SAXS results of antimiR-PNAs encapsulated in NDs. All the curves start with the Guinier region which reciprocally correlates with the size of the nanocarriers. The broad peaks at 0.07-0.2 1/Å belong to the headgroup distance of the phospholipid bilayers and bilayer thickness. Higher q peaks correlate with the internal nanostructures of the NDs. Below, best fitting results are shown for each sample. As shown, to make a clear comparison, the results for the pristine NDs are also plotted versus the ND-PNA nanocomplexes.

SAXS analysis allows structural characterizations through simulating the electron density distribution of formulated bicelles. SAXS measurements were performed on pristine bicelles, PNA-155-loaded and PNA-210-loaded bicelles with different PNA:lipid ratios and surface charges as shown in FIG. 5. The lipid concentration of all samples is 1.0 wt. %. In all the PNA encapsulated bicelles, the general scattering feature contains a broad peak between $q=0.06$ and $0.20$ Å$^{-1}$, originated from the regular spacing between the phosphate headgroups of the two leaflets where the electron density is higher than that of the acyl chains. Therefore, the electron density profile across the bilayer (i.e., water-head group shell-hydrocarbon core-head group shell-water) can be considered as a "square well". The broad peak in all SAXS patterns suggests that the lipids remain a bilayer structure.

A core-shell discoidal model (CSD model) is employed to describe the NDs, where the core and shell represent the hydrophobic lipid tails and hydrophilic phosphate headgroups, respectively. The best fitting parameters used in the model for the SAXS data listed in Table 1. $R_{core}$ and $\rho_{core}$ represent the radius and the electron density of the hydrophobic core, respectively, while $t_{shell}$ and $\rho_{shell}$ are the thickness and electron density of phosphate shells along normal of the bilayer, respectively. The rim has a thickness and electron density of $t_{rim}$ and $\rho_{rim}$, respectively. The electron density of water, $\rho_w$ is fixed throughout the fitting procedure. Moreover, the best fitting $t_{shell}$ did not vary and thus was kept constant as well. The initial guesses of the electron densities used in the model were from the literature values for lipid bilayer nanoparticles elsewhere. The CSD model can describe SAXS data well in q-range between 0.005 and 0.35 Å$^{-1}$. SAXS data at higher q values involve detailed structures in the bilayer (e.g., the contrast between methylene and methyl groups) smaller than 1.8 nm which is not considered in the current model. Although the SAXS data of bicelles (referred as to be "ND" representing nanodiscs) and PNA-loaded NDs seem to be similar. The com- The most drastic structural variation is the increase of total diameters for PNA-loaded ND, changing from 244 Å to 300 to approximately 400 Å presumably caused by two factors: enlarged $R_{core}$ and $t_{rim1}$. The best fitting results show that $R_{core}$ has less than 50% of increase while $t_{rim}$ increases by more than 70%. Most interestingly, the best fitting shell ($t_{shell}$) and ($t_{core}$) thicknesses are practically invariant. Further analysis on the best fitting $t_{rim}$ (data not shown) suggests that the range of $t_{rim}$ has to be larger than 45 Å for all PNA-loaded NDs (50-55 Å for ND PNA 210 at 1:500, 45-51 Å for PNA 210 at 1:2500 and 48-55 for PNA 155 at 1:2500). The invariant bilayer thickness ($2t_{shell}+t_{core}$) and significant increase of $t_{rim}$ suggest that the entrapped PNA molecules are mainly located at the rim of the ND. A reasonable explanation is that the hydrophobic portion of the PNA (the highly lipophilic TAMRA group) anchors into the bicelle rim, resulting in the noticeable increase of rim thickness and the planar bilayer of the discs remains unchanged as the pristine bicelles.

Example 4: Cellular Uptake Studies

Figure 6:
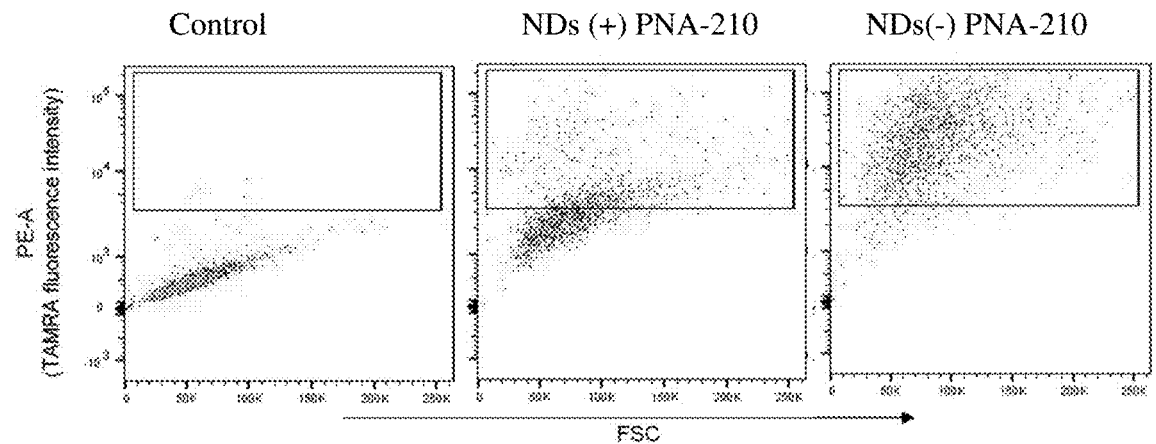
FIG. 6 shows a FACS analysis of HeLa cells following incubation with the negative ND (−) and positive ND (+) containing PNA-210. 2000 cells were selected for the number of events.
Figure 7:
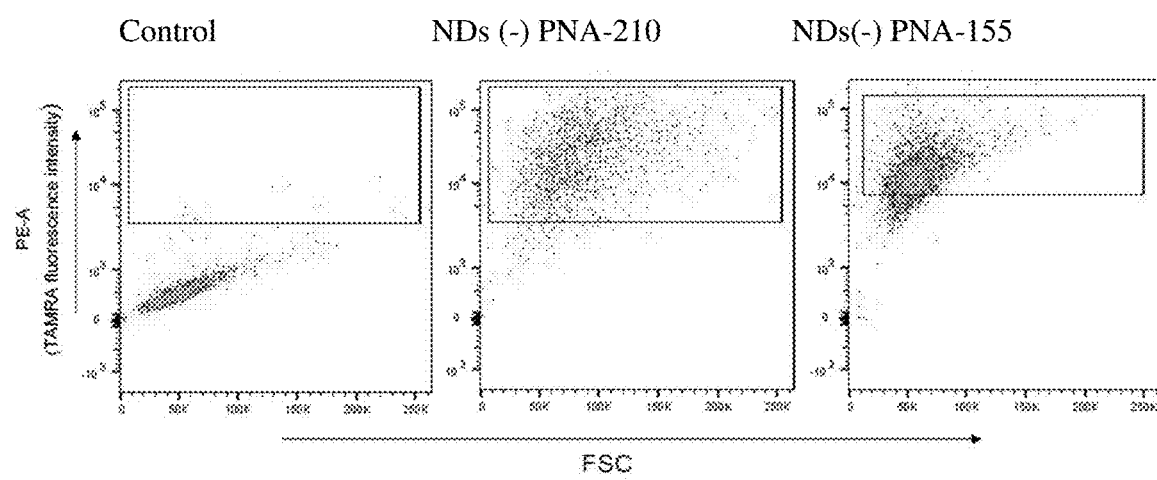
FIG. 7 shows a FACS analysis of HeLa cells following incubation with the negative ND (−) containing PNA-210 and PNA-155. 5000 cells were selected for the number of events.

Further, cellular uptake of formulated NDs was tested using TAMRA conjugated PNA-155 and PNA-210 antimiRs. Flow cytometry analysis was performed to quantify cellular uptake. HeLa cells were treated with positively as well as negatively charged bicelles containing antimiR PNAs (PNA:lipid molar ratio of 1:2500) for 24 h followed by flow cytometry analysis. The percentage of cells exhibiting fluorescence was significantly higher in the case negatively charged bicelles (approximately 95%) as compared to positively charged one (approximately 43%) (FIG. 6). Without being held to theory, it is believed that due to the morphological difference, i.e., small uniform discoidal bicelles (negatively charged) compared to a mixture of bicelles and vesicles (positively charged). In addition, the fluorescence signal was significantly higher in cells (higher cellular uptake) treated with negatively charged bicelles containing PNA-155-TAMRA as well as PNA-210-TAMRA (FIGS. 6 and 7). No auto fluorescence was observed in the un-transfected cells in the TAMRA channel.

Figure 8:
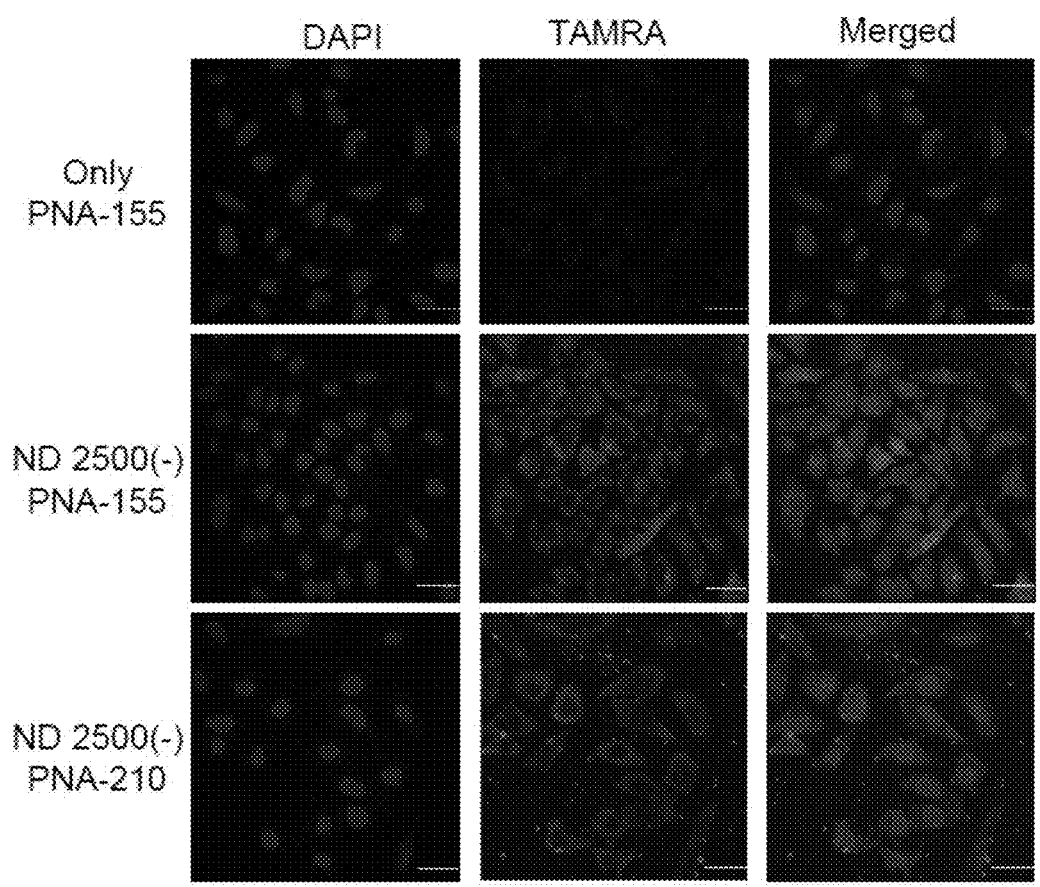
FIG. 8 shows fluorescent images of HeLa cells incubated with negative charge containing NDs for 24 h, followed by brief washing with PBS and incubation with DAPI (Nuclear staining). Blue: nucleus (DAPI), Red: PNA (TAMRA).

Next, cellular uptake of negatively charged NDs containing PNA-155-TAMRA and PNA-210-TAMRA was confirmed using confocal microscopy. HeLa cells treated with PNA-155-TAMRA and PNA-210-TAMRA alone (same dose as present in the PNA-210 and PNA-155 NDs) were used as control. HeLa cells in logarithmic phase were cultured in complete media and incubated with NDs. After 24 h of incubation, cells were briefly washed three times with buffer saline and stained with nuclear dyes followed by imaging. As shown in FIG. 8, NDs containing PNA-155-TAMRA and PNA-210-TAMRA showed a narrow distribution of TAMRA signal in comparison to antimiR PNAs alone. Moreover, significant fluorescence was observed in the nuclei of cells treated with NDs containing PNA-TAMRAs. In parallel, cellular uptake analysis of PLGA nanoparticles containing antimiR PNA-155-TAMRA was also performed in HeLa cells. NDs showed not only a dramatic increase but also more uniform uptake as compared to punctate distribution by PLGA NPs (data not shown). Together, these results show that negatively charged bicelles contribute to uniform and high transfection efficiency of antimiR PNAs in the cells. In order to assess the toxicity of bicelles, an MTT assay was performed on Human embryonic kidney (HEK) 293 primary cells. Minimal toxicity is shown as compared to the control samples (untreated and treated with pristine bicelles) (data not shown). In addition, the cellular uptake mechanism of negatively charged NDs containing antimiR PNA-155-TAMRA was also investigated.

Example 6: Mechanism of Cellular Uptake

Comprehensive studies were performed to understand the cellular uptake mechanism of negatively charged NDs containing antimiR PNAs. First, if endocytosis plays a significant role in the NDs containing antimiR PNAs was investigated by performing temperature (37° C. vs 4° C.) dependent cellular uptake studies in HeLa cells. It has been proven that low temperature (4° C.) inhibits the endocytosis-based transport across the cell membrane. The confocal microscopy and flow cytometry results revealed that NDs cellular uptake decreased significantly at 4° C. (data not shown).

Further, three pharmacological inhibitors of major endocytic pathway were used to study the cellular uptake mechanisms of negatively charged NDs containing antimiR PNAs-155 in HeLa cells. Amiloride was used to inhibit the membrane ruffling and macropinocytosis. Chlorpromazine (CPZ) was employed to block clathrin mediated endocytosis. Genistein was tested to inhibit clathrin independent endocytosis or caveolae mediated endocytosis. Inhibitor concentrations were adjusted to achieve maximum viability of HeLa cells (~95%) for 2 hours. Both flow cytometry analysis as well as confocal microscopy were used to evaluate the cellular uptake after treatment with inhibitors and bicelles. The results indicate that negatively charged NDs undergo cellular uptake by multiple endocytotic pathways. The majority of NDs containing antimiR PNAs underwent endocytosis by caveolae mediated endocytosis as well as macropinocytosis followed by clathrin mediated endocytosis (data not shown).

Example 7: Quantification of ANTIMIR Activity of NDs in Cell Culture

Figure 9:
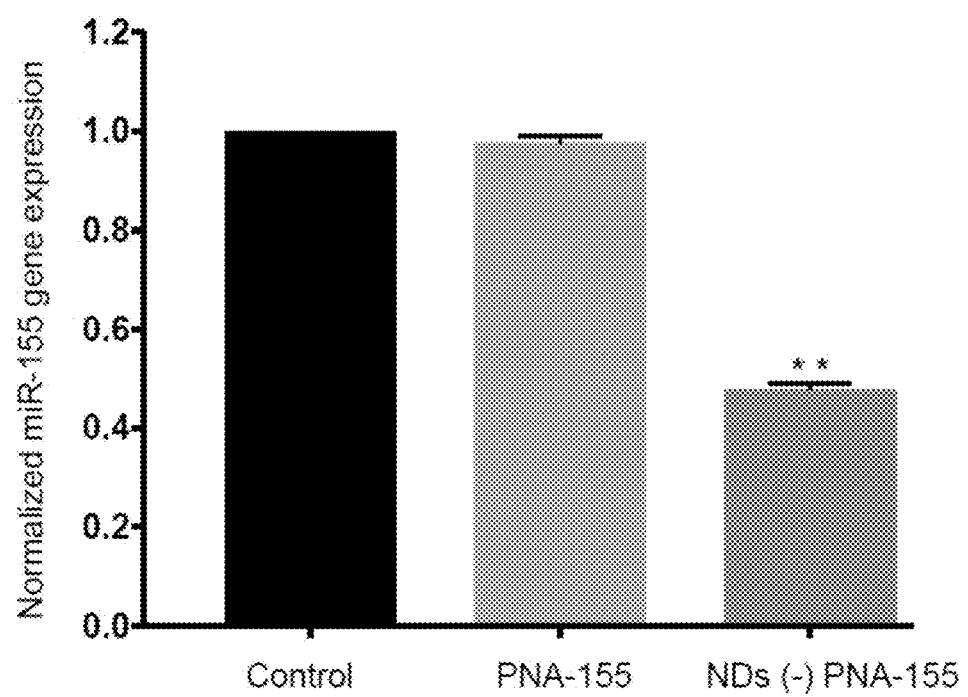
FIG. 9 shows miR-155 expression in HeLa cells after treatment with negative charge NDs containing PNA-155. miR-155 expression relative to average control.

Next, the antimiR-155 efficacy of formulated NDs was investigated by quantitative RT-PCR analysis. For all experiments, cells treated with PNA-155 alone were used as controls. The expression of miR-155 in HeLa cell lines was tested using RT-PCR. HeLa cells exhibited overexpression of miR-155 and hence, HeLa cell lines were tested for comparing the efficacy of formulated negatively charged NDs containing PNA-155 at PNA:lipid molar ratio of 1:2500. HeLa cells were treated with sufficient amount of negatively charged NDs to achieve a dose of 4 μM PNA for 24 h. RNA was extracted and quantified by RT-PCR using U6 as a control. Unlike the control, PNA-155-TAMRA loaded negatively charged NDs reduced miR-155 expression by approximately 50% (FIG. 9). These results signify the antimiR activity of NDs containing antimiR PNAs. Further, the antimiR-155 effect was measured at protein levels using western blot analysis. p53 acts as a tumor suppressor and regulates cell division by inhibiting cells from growing and fast proliferating in an uncontrolled way. It has been well established that miR-155 upregulation decreases level of p53 protein. The results revealed that pretreatment of HeLa cells led to approximately 39% upregulation of p53 (data not shown).

DISCUSSION

While the use of PNAs was reported more than three decades ago, cellular uptake of PNAs still circumscribes their broader clinical applications. Using comprehensive structural and biophysical characterizations, fluorescence, as well as functional cell-based assays, it is demonstrated herein that lipid-based formulations can be used for delivery of therapeutically active PNAs. It is noteworthy that the lipids (PEG 2000-DSPE, DPPG DPPC and DHPC) used to constitute the NDs are FDA-approved. A series of positive and negative charge NDs containing different PNA:Lipid molar ratio were tested. The results indicate that negatively charged bicelles containing a 1:2500 molar ratio of PNA:Lipid (the least disturbed composition) exhibit uniform size as well as discoidal shape. First, it was confirmed that 1:2500 ratio results in maximum encapsulation efficiency of two antimiRs, i.e., PNA-210 and PNA-155. NDs made of lipid with controlled size are attainable. The PEGylated NDs are very stable and only turn into vesicles of similar size through incubating at 55° C. or above for several hours, confirmed by TEM, DLS, and SAXS. They have long-term stability in aqueous solutions and therefore are suitable as delivery carriers for drugs, vaccines, and genes for a variety of diseases.

The non-spherical geometries such as rod-like and discoidal nanoparticles have been proven to permeate deeper in mammary tumors greater than their spherical counterparts with similar hydrodynamic sizes. It has also been reported that NDs have high diffusion and penetration properties in collagen-rich environment. Presumably, the small dimension along their thickness dimension promotes the tumor penetration as compared with the symmetric structure of vesicles. Interestingly, recent mathematical modeling combined with in vitro and ex-vivo experimentation demonstrated that discoidal geometries possessed the most favorable margination dynamics in the body. Additionally, discoidal NPs show particular movement dynamics that favor the interaction with vessel wall more than spherical particles. Though it has been demonstrated that positively charged NPs are internalized into cell favorably due to their strong interaction with the negatively charged phospholipid components of the cell membrane, their toxicity is also much higher. Hence, the negatively charged bicelles are also favorable in terms of safety as well as efficacy. The cell culture analysis did not show any noticeable toxicity.

Further, the morphology of PNA/NDs was investigated using SAXS data analysis. The parameters of the Core-Shell Bicelle model, that best fits the SAXS data of bicelles, indicate axial shell thickness, radial shell thickness, core thickness and radius consistent with literature values for pristine bicelles. No significant difference was found in the SAXS patterns of PNAs loaded NDs (i.e., discoidal shape with invariant bilayer thickness) compared to that of the pristine bicelle except that the Guinier regime shifts to the lower q values, indicative of larger particles. The drastically increased rim thickness suggests that most of the entrapped PNAs are preferably localized at the rim region. The disc rim mainly composed of short-chain DHPC has a large spontaneous curvature and contains more defects, making it suitable to accommodate higher-curvature objects like large PNA ending domains. Cell culture analysis substantiates that negatively charges bicelles show high transfection efficiency. No punctuated structure in the HeLa cells treated with bicelles was identified indicating that a good portion of bicelles may not undergo endosomal entrapment and uniformly distribute the antimiR PNAs in the cells. In addition, that the fact that the negatively charged bicelles undergo cellular uptake by multiple endocytic mechanisms is also advantageous.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

---

The invention claimed is:

1. A self-assembled discoidal PNA delivery vehicle, comprising
 a zwitterionic short chain 6:0 dihexanoyl phosphatidylcholine (DHPC);
 a zwitterionic long chain 16:0 zwitterionic dipalmitoyl phosphatidylcholine (DPPC);
 a charged long chain 16:0 zwitterionic dipalmitoyl phosphatidylglycerol (DPPG);
 a polyethylene glycol (PEG2000)-conjugated distearoyl phosphoethanolamine (DSPE-PEG2000),
 wherein the DPPC:DHPC:DPPG:DSPE-PEG2000 molar ratio is 69.58:25.1:3.76:2.0; and
 an encapsulated PNA molecule.

2. The self-assembled discoidal PNA delivery vehicle of claim 1, having a diameter of 20-50 nm.

3. The self-assembled discoidal PNA delivery vehicle of claim 1, wherein the PNA comprises PNA-155 or PNA-210.

4. A one pot method of self assembling a discoidal PNA delivery vehicle comprising encapsulated PNA, comprising
 mixing
  a cosolvent;
  a zwitterionic short chain 5:0 to 7:0 diacyl lipid comprising a phosphatidylcholine or phosphatidylethanolamine hydrophilic headgroup;
  a zwitterionic long chain 14:0 to 18:0 diacyl lipid comprising a phosphatidylcholine or phosphatidylethanolamine hydrophilic headgroup;
  a charged long chain 12:0 to 18:0 diacyl lipid comprising a phosphatidylglycerol, phosphoinositol, phosphatidic acid, or phosphatidylserine hydrophilic headgroup;
  a PEGylated lipid of the formula distearoyl phosphoethanolamine (DSPE)-$PEG_n$-TG, wherein n is the molecular weight of the PEG and is 1000 to 5000, and TG is a terminal group which is hydroxyl, succinyl, cyanur, folate, maleimide, pyridoxal-5'-diphosphate (PDP), amine, biotin, trimethylsilyl (TMS), carboxylic acid, azide, dibenzocyclooctyne (DBCO), or benzylguanine; and
  the PNA molecule,
 wherein the molar ratio of the combination of the zwitterionic long chain diacyl lipid and the charged long chain diacyl lipid to the short chain diacyl lipid is 0.5 to 5,
 wherein the molar ratio of the charged long chain diacyl lipid to the zwitterionic long chain diacyl lipid is greater than 0.01,
 wherein the molar % of the PEGylated lipid to all lipids is 1% to 5%, and
 wherein the molar ratio of PNA to total lipid is 1:500 to 1:2500; and
 providing sufficient time for the discoidal PNA delivery vehicle to self assemble and encapsulate the PNA; and
 optionally removing the cosolvent.

5. The method of claim 4, wherein
 the zwitterionic short chain diacyl lipid is a dihexanoyl phosphatidylcholine (DHPC) lipid,
 the zwitterionic long chain diacyl lipid is a dipalmitoyl phosphatidylcholine (DPPC) lipid,
 the charged long chain diacyl lipid is a dipalmitoyl phosphatidylglycerol (DPPG) lipid, and
 the pegylated lipid is a PEG2000-conjugated distearoyl phosphoethanolamine (DSPE-PEG2000).

6. The method of claim 4, wherein the self-assembled discoidal PNA delivery vehicle has a diameter along the circular axis of 20-100 nm.

7. The method of claim 4, wherein the self-assembled discoidal PNA delivery vehicle has a stability of 3 months at 4° C.

8. The method of claim 4, wherein the PNA comprises a bis-PNA, a tail clamp (tc) PNA, a PNA including a G-clamp monomer, a γ-PNA, a miniPEG containing PNA comprising one or more units having a polyethyleneglycol sidechain at the γ-carbon of the PNAs backbone, or a triplex forming PNA composition comprising a Hoogsteen binding peptide nucleic acid PNA segment and a Watson-Crick binding PNA segment.

9. The method of claim 4, wherein the encapsulation efficiency of the PNA is 90%.

10. The method of claim 4, wherein the whole processing time including dissolution, evaporation and self-assembly is from 7 hours to 15 hours.

11. The method of claim 4, wherein the cosolvent is DMF or DMSO.

12. A method of enhancing cellular uptake of PNA, comprising contacting a cell with the self assembled a discoidal PNA delivery vehicle of claim 1, wherein the self assembled discoidal PNA delivery vehicle provides improved cellular uptake compared to a liposome.

13. The method of claim 12, wherein the PNA modifies expression of a gene in the cell.

14. The method of claim 12, wherein the PNA modifies expression of a gene target for cancer.

* * * * *